(12) United States Patent
Sato (10) Patent No.: US 10,041,912 B2
(45) Date of Patent: Aug. 7, 2018

(54) SOUND WAVE SENSOR (71) Applicant: KYUSHU INSTITUTE OF TECHNOLOGY, Fukuoka (JP)

(72) Inventor: Yasushi Sato, Fukuoka (JP)

(73) Assignee: KYUSHU INSTITUTE OF TECHNOLOGY, Fukuoka (JP)

( * ) Notice: Subject to any disclaimer, the term of this patent is extended or adjusted under 35 U.S.C. 154(b) by 14 days.

(21) Appl. No.: 15/127,726

(22) PCT Filed: Mar. 17, 2015

(86) PCT No.: PCT/JP2015/057828
§ 371 (c)(1),
(2) Date: Sep. 20, 2016

(87) PCT Pub. No.: WO2015/141657
PCT Pub. Date: Sep. 24, 2015

(65) Prior Publication Data
US 2017/0089864 A1 Mar. 30, 2017

(30) Foreign Application Priority Data
Mar. 20, 2014 (JP) .................................. 2014-057865

(51) Int. Cl.
G07D 11/00 (2006.01)
G01H 13/00 (2006.01)
(Continued)

(52) U.S. Cl.
CPC .............. G01N 29/12 (2013.01); G01H 13/00 (2013.01); G07D 7/08 (2013.01); G07D 11/0036 (2013.01)

(58) Field of Classification Search
CPC .......... G01N 29/12; G01H 13/00; G07D 7/08; G07D 11/0036
(Continued)

(56) References Cited

U.S. PATENT DOCUMENTS 2,238,668 A * 4/1941 Wellenstein ............. G10K 5/00
116/137 A
4,568,414 A * 2/1986 Oldis ...................... H04R 19/01
156/160
(Continued)

FOREIGN PATENT DOCUMENTS

JP S61-256213 A 11/1986
JP H01-098922 A 4/1989
(Continued)

OTHER PUBLICATIONS

International Search Report issued in Application No. PCT/JP2015/057828, dated Jun. 16, 2015.

*Primary Examiner* — J M Saint Surin
(74) *Attorney, Agent, or Firm* — Michael Best & Friedrich LLP (57) ABSTRACT

A sound wave sensor, capable of reliably detecting presence or absence of a banknote very easily with use of sound waves, is provided. The sound wave sensor includes a sounding body 2 that outputs a sound wave signal of a predetermined frequency, an echo body 3 opposed to the sounding body 2 in a direction in which the sounding body 2 outputs the sound wave signal, the echo body 3 being provided at a position where the sound wave signal resonates at the predetermined frequency; a slit 5 through which a sheet-like banknote 4 passes, the slit 5 being provided between the sounding body 2 and the echo body 3; and a resonance determination unit 6 that determines a resonant state of the frequency output from the sounding body 2. The resonance determination unit 6 determines a resonant state by detecting variation in power consumption of the sounding body 2.

6 Claims, 9 Drawing Sheets

(51) Int. Cl.
*G07D 7/08* (2006.01)
*G01N 29/12* (2006.01)

(58) Field of Classification Search
USPC .......................................................... 73/627
See application file for complete search history.

(56) References Cited

U.S. PATENT DOCUMENTS

| | | | | |
|---|---|---|---|---|
| 5,023,846 | A * | 6/1991 | Busch-Sorensen | .... G01B 17/02 |
| | | | | 340/675 |
| 6,543,288 | B1 * | 4/2003 | Blouin | .................... G01L 5/042 |
| | | | | 73/159 |
| 6,745,628 | B2 * | 6/2004 | Wunderer | .............. G01N 29/11 |
| | | | | 73/159 |
| 2003/0183012 | A1 * | 10/2003 | Wunderer | .............. G01B 17/02 |
| | | | | 73/602 |
| 2005/0087010 | A1 * | 4/2005 | Nojiri | .................... B41J 11/009 |
| | | | | 73/159 |
| 2011/0226061 | A1 * | 9/2011 | Itsumi | ...................... B65H 7/02 |
| | | | | 73/589 |

FOREIGN PATENT DOCUMENTS

| | | | |
|---|---|---|---|
| JP | 09053978 | * | 2/1997 |
| JP | 2010-032242 A | | 2/2010 |
| WO | WO-2008/105291 A1 | | 9/2008 |

\* cited by examiner

SOUND WAVE SENSOR

TECHNICAL FIELD

The present invention relates to a sound wave sensor that detects a sheet-like medium with use of a change in the resonance frequency of sound waves.

BACKGROUND ART

Figure 9:
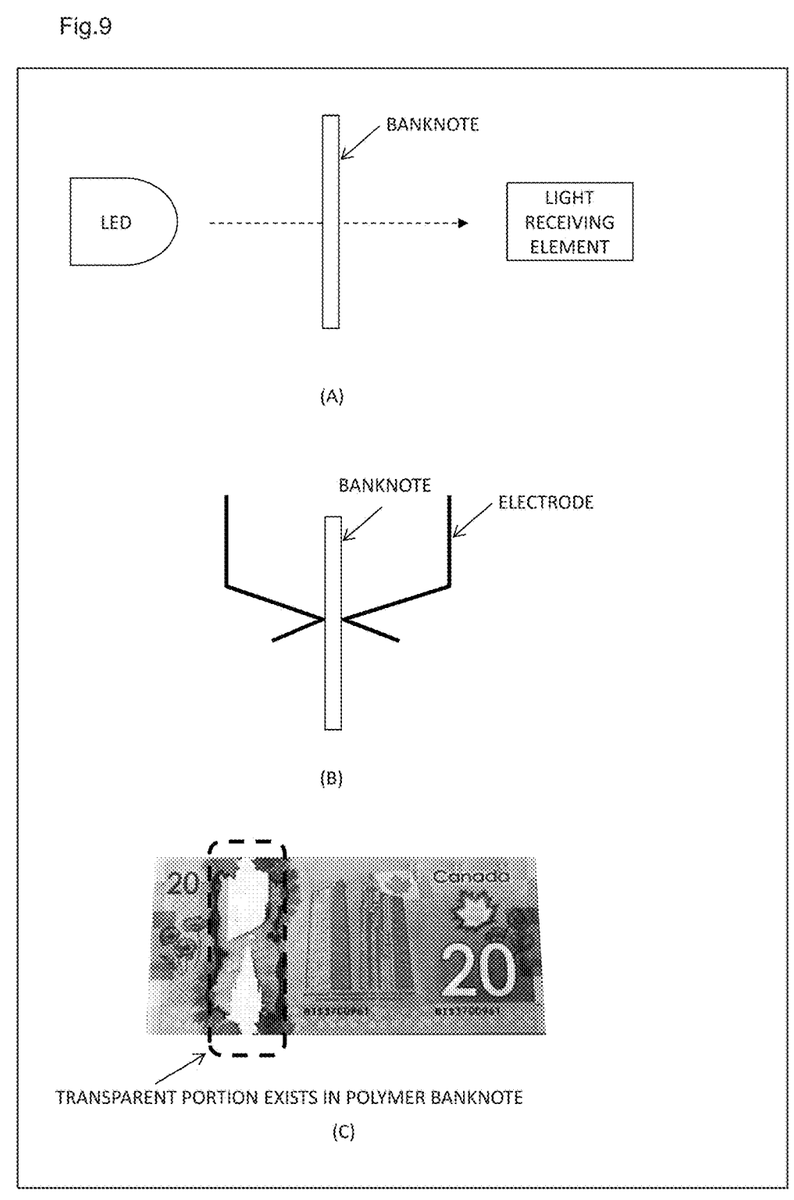
FIG. 9 is a schematic diagram illustrating a method of detecting a banknote in a conventional ATM.

Optical sensor is often used for counting the number of banknotes in an automatic teller machine (ATM) or the like, for example. FIG. 9 schematically illustrates a method of detecting a banknote in a conventional ATM. As illustrated in FIG. 9(A), in a conventional method, a banknote is detected when the LED light is interrupted by the banknote. This method is widely used in general because presence or absence of a banknote can be detected in a contactless manner. However, a trouble occurs in the case of a foreign banknote as illustrated in FIG. 9(C).

That is, regarding a foreign banknote, a Polymer banknote is used recently in order to enhance durability. In the case of a design-conscious banknote as illustrated in FIG. 9(C), there is a transparent portion in the banknote whereby a problem of misdetection occurs. In other words, since a transparent portion transmits light from an LED, it may be erroneously recognized that there is no banknote.

As a method of preventing such misdetection, a resistance measuring method is known (see FIG. 9(B)). In this method, electrodes are brought into contact with each other, and by allowing a banknote to pass between the contacting electrodes, interruption of a connection between the electrodes is detected. In this method, even in the case of a banknote with a transparent portion as described above, presence or absence thereof can be detected reliably. However, since a banknote must be in contact with electrodes, there is a problem that the banknote is damaged.

Further, as a technology of detecting banknote fatigue with use of ultrasonic waves, there is a technology disclosed in Patent Literature 1, for example. The technology disclosed in Patent Literature 1 is a medium fatigue detection device including an ultrasonic wave transmission element (11) that oscillates ultrasonic waves as burst waves, an ultrasonic wave receiving element (12), and a receiver sensitivity detection unit (22). The elements (11) and (12) are arranged at positions opposite to each other via a sheet-like medium (5) such as a banknote passing between the both elements. Ultrasonic waves transmitted from the element (11) are made incident on the main surface of the sheet-like medium (5) at a predetermined incident angle θ. By measuring the variation in the receiver sensitivity of the ultrasonic waves passing through the sheet-like medium (5), fatigue of the medium (5) is detected.

CITATION LIST

Patent Literature

Patent Literature 1: International Publication No. WO 2008/105291

SUMMARY OF INVENTION

Technical Problem

However, the technology disclosed in Patent Literature 1 needs to have a receiving element at an opposite position via a banknote, and to regulate the relationship between the receiving element and the transmission element to have an incident angle θ, for example, which makes the configuration and the setting of the device complicated. Further, since medium fatigue is detected in the technology of Patent Literature 1, a very strict computing function or the like is required, which increases labor and cost for manufacturing a device.

The present invention provides a sound wave sensor capable of reliably detecting presence or absence of a banknote very easily with use of sound waves.

Solution to Problem

A sound wave sensor according to the present invention includes a sounding body that outputs a sound wave signal of a predetermined frequency; an echo body opposed to the sounding body in a direction in which the sounding body outputs the sound wave signal, the echo body being provided at a position where the sound wave signal resonates at the predetermined frequency; a slit through which a sheet-like medium passes, the slit being provided between the sounding body and the echo body; and determination means for determining a resonant state of the frequency output from the sounding body.

As described above, the sound wave sensor according to the present invention includes a sounding body that outputs a sound wave signal of a predetermined frequency; an echo body opposed to the sounding body in a direction in which the sounding body outputs the sound wave signal, the echo body being provided at a position where the sound wave signal resonates at the predetermined frequency; a slit through which a sheet-like medium passes, the slit being provided between the sounding body and the echo body; and determination means for determining a resonant state of the frequency output from the sounding body. Hence, when a sheet-like medium such as a banknote passes thorough the slit, for example, it is possible to reliably detect presence of the medium by measuring only a change in the resonance frequency. Thus, the sound wave sensor of the present invention has an advantageous effect that a medium can be detected very easily and reliably.

Further, since measurement is taken only on the resonance frequency, there is no need to provide a receiving element or the like. An advantageous effect that a device structure can be simplified is thus achieved.

In the sound wave sensor according to the present invention, the determination means determines the resonant state by detecting variation in power consumption of the sounding body.

As described above, the sound wave sensor of the present invention determines the resonant state by detecting variation in power consumption of the sounding body. Thus, the sound wave sensor of the present invention has an advantageous effect that a medium can be detected reliably by only measuring power consumption of the sounding body, without a receiving element or the like.

The sound wave sensor of the present invention includes a microphone that is provided near the sounding body and receives the sound wave signal output from the sounding body. The determination means determines the resonate state based on the sound pressure of a signal detected by the microphone.

As described above, the sound wave sensor of the present invention includes a microphone that is provided near the sounding body and receives the sound wave signal output from the sounding body, and the determination means determines the resonate state based on the sound pressure of a signal detected by the microphone. Thus, the sound wave sensor of the present invention has an advantageous effect that a medium can be detected very easily and reliably.

The sound wave sensor of the present invention includes a first casing for accommodating the sounding body. An output hole through which the sound wave from the sounding body is output is formed in a surface opposed to a surface to which the sounding body is provided in the first casing.

As described above, the sound wave sensor of the present invention includes a first casing for accommodating the sounding body. An output hole through which the sound wave from the sounding body is output is formed in a surface opposed to a surface to which the sounding body is provided in the first casing. Thus, the sound wave sensor of the present invention has an advantageous effect that only sound waves of the resonance frequency can be output reliably while excluding influence of the noise from the outside.

Further, since the sounding body is accommodated in the casing, a distance between a medium passing through the slit and the sounding body can be maintained stably. An advantageous effect that a change in the resonance frequency can be detected reliably is thus achieved.

The sound wave sensor of the present invention includes a second casing opposed to the surface of the first casing in which the output hole is formed. The second casing includes a surface having an input hole through which the sound wave output from the output hole is input, and the second casing functions as the echo body.

As described above, the sound wave sensor of the present invention includes a second casing opposed to the surface of the first casing in which the output hole is formed. The second casing includes a surface having an input hole through which the sound wave output from the output hole is input, and the second casing functions as the echo body. Therefore, influence of the noise from the outside can be excluded, and a distance between a medium passing through the slit and the echo body can be maintained stably. An advantageous effect that a change in the resonance frequency can be detected reliably is thus achieved.

In the sound wave sensor of the present invention, the sound waves are ultrasonic waves.

As described above, the sound wave sensor of the present invention uses ultrasonic waves to detect presence of a medium. Therefore, the sound wave sensor of the present invention has an advantageous effect that the device can be used quietly in an inaudible manner. Further, since ultrasonic waves have high directivity, an advantageous effect that sound waves can be output linearly and reliably to the slit, through which a medium passes, is achieved.

DESCRIPTION OF EMBODIMENTS

Hereinafter, embodiments of the present invention will be described. The same elements are denoted by the same reference numerals throughout the embodiments.

First Embodiment of the Present Invention

A sound wave sensor according to the present embodiment will be described using FIGS. 1 to 6. The sound wave sensor of the present embodiment determines presence or absence of a target object by measuring a change in the resonance of sound waves. In the embodiment below, description will be given in which a target object is a banknote. To detect presence or absence of a banknote, a detection method using light is generally used, as described above. However, some types of banknotes include a transparent area, which can lead to inconvenience. The sound wave sensor of the present embodiment detects a banknote using resonance of sound waves. For this reason, the sensor is suitable for a device in which extremely accurate and high-speed counting of banknotes is required, such as an ATM, for example.

Figure 1:
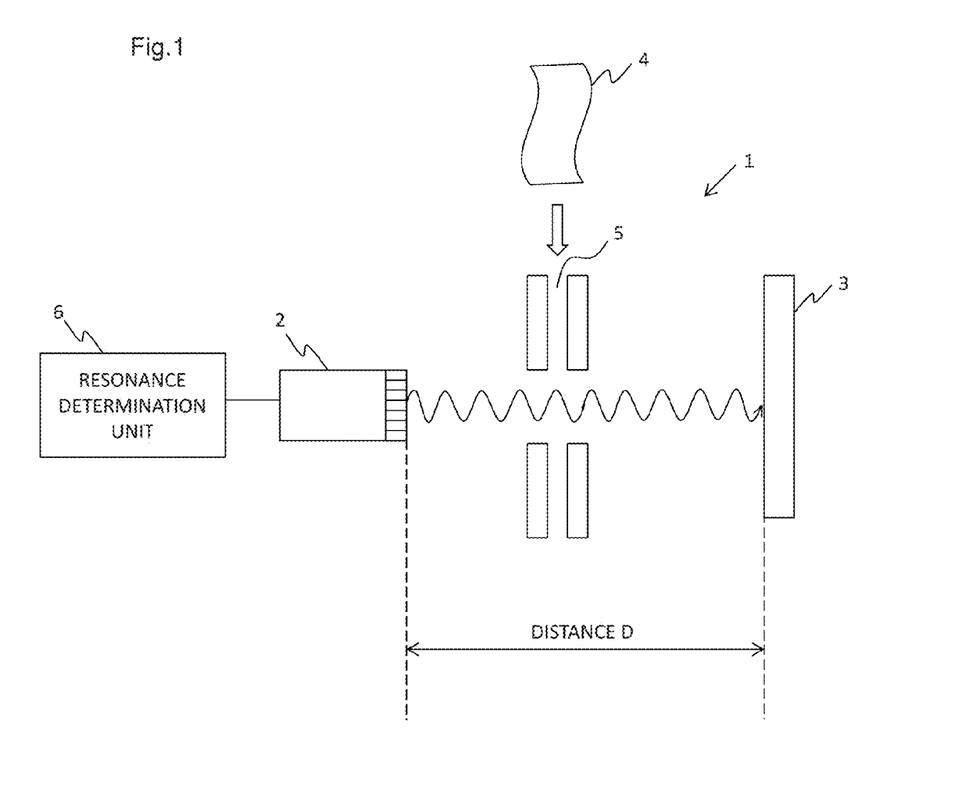
FIG. 1 is a schematic diagram illustrating a configuration when an object is not detected by a sound wave sensor according to a first embodiment.

FIG. 1 is a schematic diagram illustrating a configuration when an object is not detected by the sound wave sensor of the present embodiment. A sound wave sensor 1 according to the present embodiment includes a sounding body 2 that outputs sound waves of a predetermined frequency (about 10 kHz, for example), an echo body 3 provided at a position where sound waves output from the sounding body 2 resonate at the predetermined frequency having been set, a slit 5, provided between the sounding body 2 and the echo body 3, through which a banknote 4 which is an object passes, and a resonance determination unit 6 that determines a resonate state of the sounding body 2. It should be noted that as sound waves, it is possible to use ultrasonic waves which are sound waves having a high frequency of a level that a person having ordinary hearing ability does not feel a sense of hearing (for example, sound waves having a frequency of about 20 kHz or higher).

Figure 2:
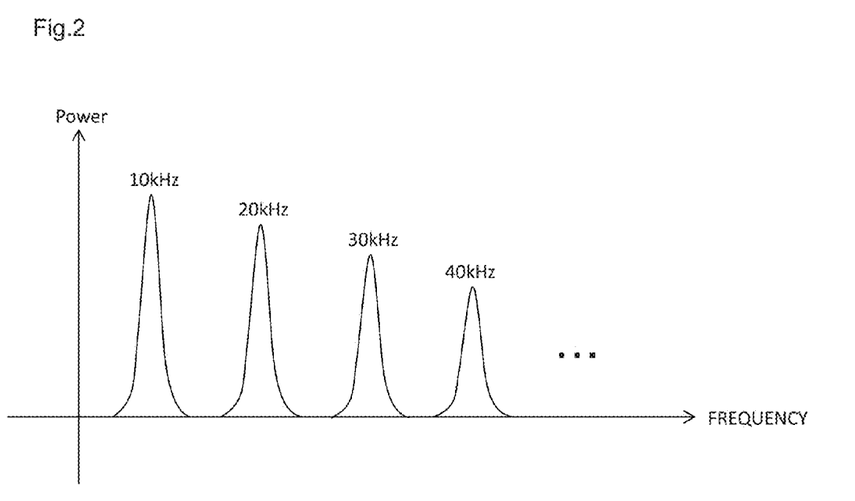
FIG. 2 is a diagram illustrating a resonance characteristic in the case of FIG. 1.

From the sounding body 2, sound waves of 10 kHz are output, for example, and the echo body 3 is provided at a position of a distance D where the echo body 3 resonates at just 10 kHz. The frequency characteristic at this time takes a waveform as illustrated in FIG. 2. That is, a frequency characteristic in which peaks appear at positions of the oscillation frequency (10 kHz) and high harmonic waves thereof (frequencies of integer multiple of 10 kHz (10 kHz, 20 kHz, . . . )) is measured.

A standby state where an ATM or the like does not operate particularly is a state where resonance occurs with a resonance characteristic as illustrated in FIG. 2. Thus, power consumption is extremely low, which leads to energy saving.

Figure 3:
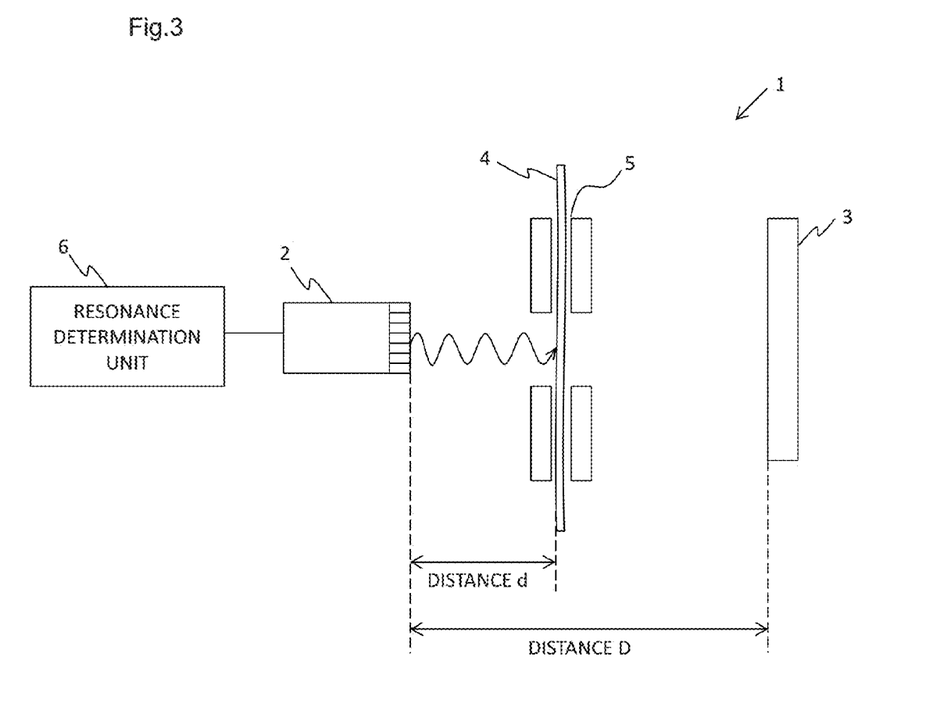
FIG. 3 is a schematic diagram illustrating a configuration when an object is detected by the sound wave sensor according to the first embodiment.

FIG. 3 is a schematic diagram illustrating a configuration when an object is detected by the sound wave sensor according to the present embodiment. The configuration of the sound wave sensor 1 is the same as that of FIG. 1, and the banknote 4 is in a state of passing through the slit 5. That is, the banknotes 4 are passing through the slit 5 one by one when the banknotes 4 are counted for deposit or withdrawal in an ATM or the like, for example, and a passing state is shown.

Figure 4:
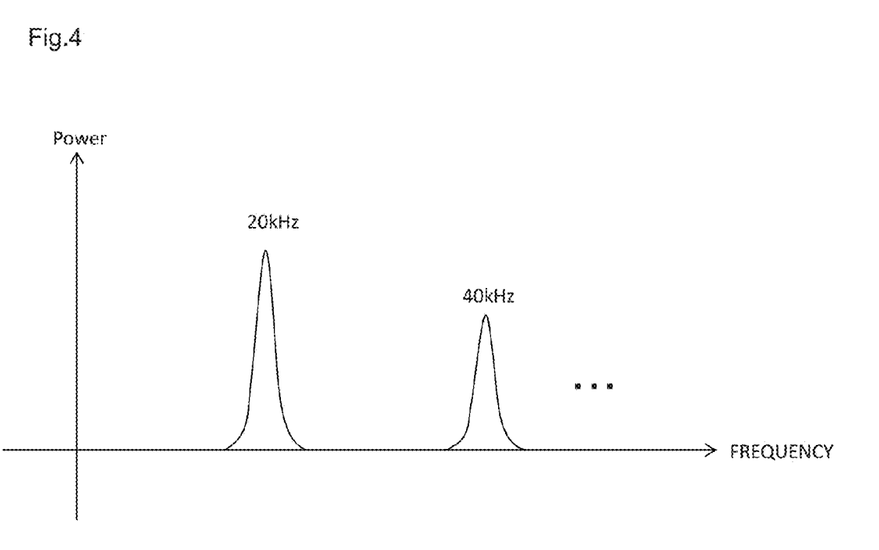
FIG. 4 is a diagram illustrating a resonance characteristic in the case of FIG. 3.

As illustrated in FIG. 3, when the banknote 4 passes through the slit 5 from the state illustrated in FIG. 1, the distance D from the sounding body 2 to the echo body 3 is changed to a distance d from the sounding body 2 to the banknote 4. Along with it, the resonant state is changed. FIG. 4 is a diagram illustrating an exemplary waveform when the resonant state is changed from the state illustrated in FIG. 2. In the case of FIG. 4, since the banknote 4 exists in the slit 5, a resonance peak appears at 20 kHz, and peaks appear in higher harmonic waves thereof (frequencies of integer multiple of 20 kHz (40 kHz, 60 kHz, . . . )).

Specifically, the resonance characteristic largely differs between the case where the banknote 4 is passing through the slit 5 and the case of not passing, as illustrated in FIG. 2 and FIG. 4. By analyzing a change in the resonance characteristic by the resonance determination unit 6, it is possible to determine presence or absence of the banknote 4. As is clear from the waveforms in FIG. 2 and FIG. 4, resonance does not occur at 10 kHz when the banknote 4 is passing through the slit 5. Thus, the resonance determination unit 6 only needs to detect resonance characteristics at a predetermined frequency (10 kHz in this case) having been set.

With this configuration, even in the case of the banknote 4 having a transparent portion as illustrated in FIG. 9(C), presence or absence thereof can be detected reliably as a single banknote 4.

Figure 5:
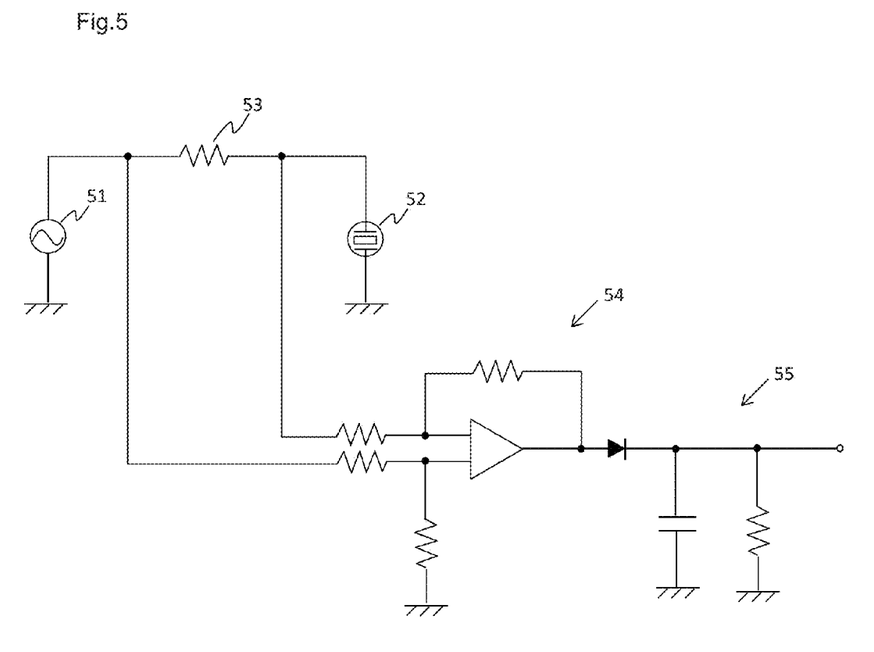
FIG. 5 is a circuit diagram of the sound wave sensor according to the first embodiment.

FIG. 5 is a circuit diagram of the sound wave sensor according to the present embodiment. An oscillator 51 and a piezoelectric element 52 constitute the sounding body 2 that outputs sound waves of a predetermined frequency (10 kHz, for example). A change in power consumption between them (a change in the consumed electric current flowing in a resistance 53) is measured via an amplifier circuit 54 and a filter circuit 55. When it resonates at a predetermined frequency, power consumption is extremely low. However, when it does not resonate at a predetermined frequency, power consumption increases. Therefore, by measuring such changes, it is possible to determine a resonant state.

Figure 6:
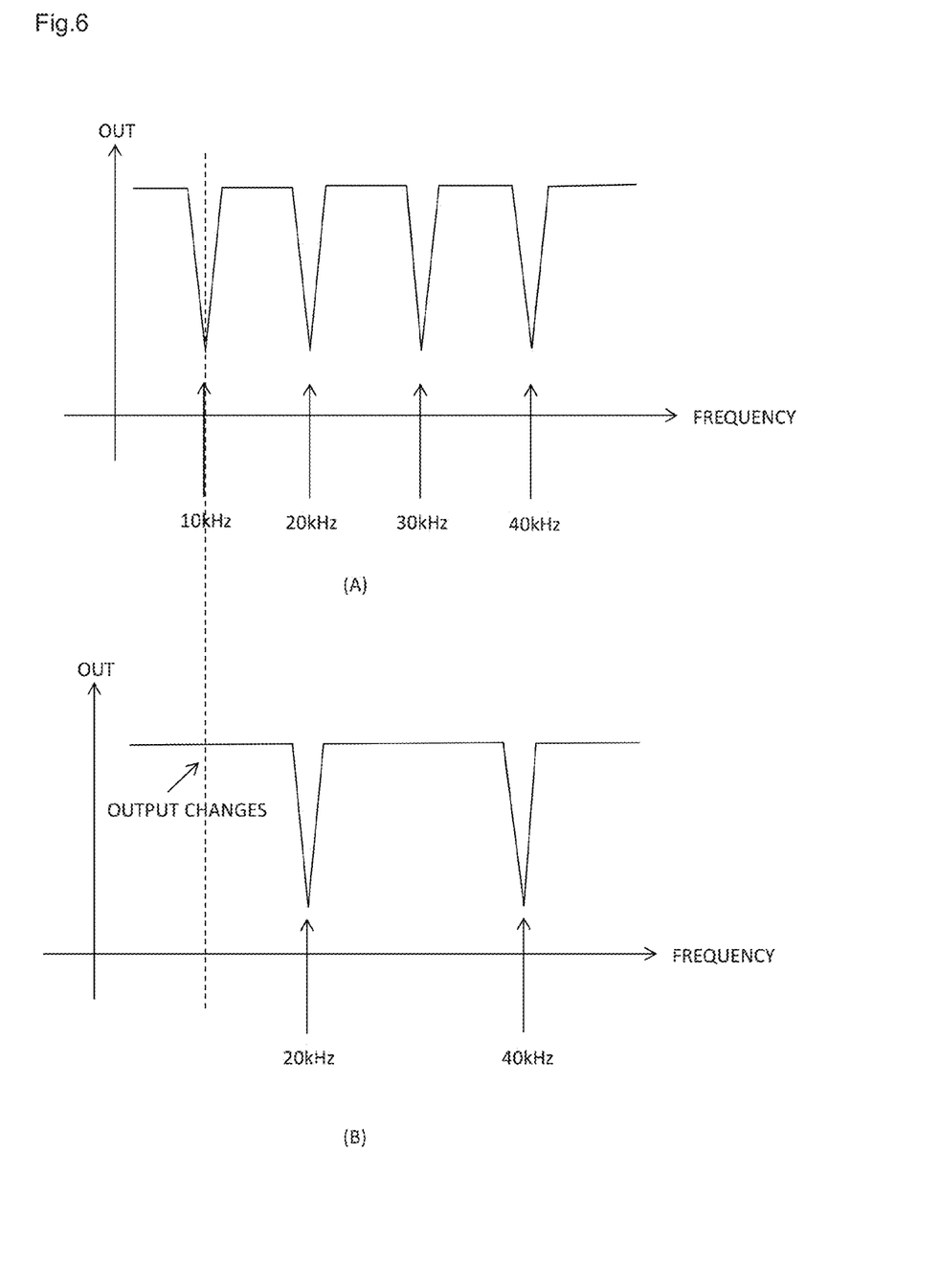
FIG. 6 is a diagram illustrating a relationship between frequency and power consumption in the sound wave sensor according to the first embodiment.

FIG. 6 is a diagram illustrating a relationship between the frequency and power consumption in the sound wave sensor according to the present embodiment. FIG. 6(A) is a diagram illustrating the case where the banknote 4 is not passing through the slit 5, and FIG. 6(B) is a diagram illustrating the case where the banknote 4 is passing through the slit 5. When the banknote 4 is not passing through the slit 5 and resonance occurs at a predetermined frequency (10 kHz, for example) having been set, as illustrated in FIG. 6(A), power consumption of the sounding body 2 at the resonance frequency and higher harmonic waves extremely decreases. When the banknote 4 is passing through the slit 5, the resonance frequency is changed. Thus, as illustrated in FIG. 6(B), power consumption at 10 kHz is larger compared with the case illustrated in FIG. 6(A). This means that the resonance determination unit 6 performs determination by detecting only a change in power consumption at 10 kHz in which the change can be observed, whereby presence or absence of the banknote 4 is determined accurately one by one.

As described above, the sound wave sensor 1 of the present embodiment is configured such that when a sheet-like medium such as a banknote passes through the slit, for example, it measures only a change in the resonance frequency to thereby be able to detect presence of the medium reliably, whereby it is possible to detect the medium very easily and reliably. Further, since measurement is taken on the resonance frequency, there is no need to provide a receiving element or the like, which enables the device configuration to be simplified.

Further, since the resonant state is determined by detecting the variation in power consumption of the sounding body 2, it is possible to detect a medium easily and reliably by only measuring power consumption of the sounding body 2.

Second Embodiment of the Present Invention

A sound wave sensor according to the present embodiment will be described with use of FIG. 7. The sound wave sensor according to the present embodiment includes a microphone 71 provided near the sounding body 2. The microphone 71 receives a sound wave signal output from the sounding body 2, and the resonance determination unit 6 determines a resonant state based on a sound pressure of the signal detected by the microphone 71.

Figure 7:
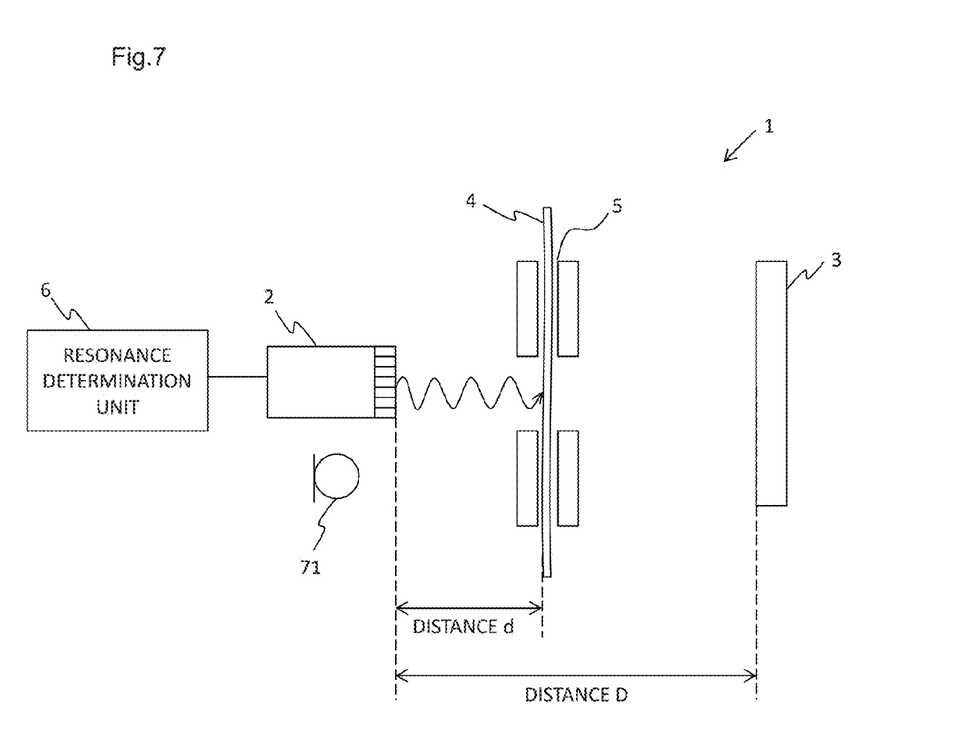
FIG. 7 is a schematic diagram illustrating a configuration of a sound wave sensor according to a second embodiment.

FIG. 7 is a schematic diagram illustrating the sound wave sensor according to the present embodiment. In FIG. 7, the sound wave sensor 1 includes a sounding body 2 that outputs sound waves of a predetermined frequency, an echo body 3 provided at a position where the sound waves output from the sounding body 2 resonate at a predetermined frequency having been set, a slit 5, provided between the sounding body 2 and the echo body 3, through which a banknote 4 which is an object passes, a microphone 71 for measuring a sound pressure of the sounding body 2, the microphone 71 being provided near the sounding body 2 in a region of a side where the sounding body 2 is disposed with reference to the slit 5, and a resonance determination unit 6 that determines a resonant state of the sounding body 2 based on the sound pressure received by the microphone 71.

When a sound wave signal oscillated by the sounding body 2 resonates at the oscillated frequency, a sound pressure is very high. Namely, in the case of FIG. 2 in the first embodiment, since the banknote 4 is not passing through the slit 5 and resonance occurs at 10 kHz, a sound pressure received by the microphone 71 is very high. On the other hand, in the case of FIG. 4 in the first embodiment, since the banknote 4 is passing through the slit 5, resonance is not made at 10 kHz, whereby a sound pressure received by the microphone 71 is very low.

Accordingly, the resonance determination unit 6 only measures a sound pressure of the microphone 71, and when there is a change in the sound pressure, the resonance determination unit 6 is able to determine that the resonance characteristic of the sound waves oscillated by the sounding body 2 is changed. This means that by only measuring a change in the sound pressure, it is possible to determine whether or not the banknote 4 is passing through the slit 5.

Third Embodiment of the Present Invention

A sound wave sensor according to the present embodiment will be described with use of FIG. 8. The sound wave sensor according to the present embodiment is configured such that the sounding body 2 is accommodated in a first casing having a hole through which sound waves are output. Further, the echo body 3 is a second casing having a hole through which the sound waves output from the first casing are input.

Figure 8:
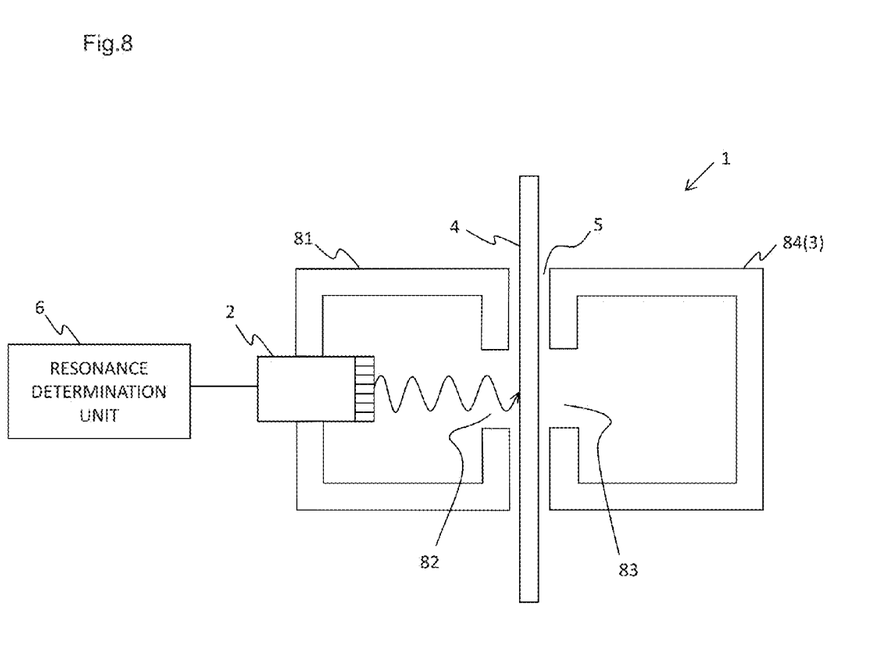
FIG. 8 is a schematic diagram illustrating a configuration of a sound wave sensor according to a third embodiment.

FIG. 8 is a schematic diagram illustrating a configuration of the sound wave sensor according to the present embodiment. In FIG. 8, the sound wave sensor 1 includes a first casing 81 that accommodates a sounding body 2. The first casing 81 is configured such that a surface, opposed to a surface to which the sounding body 2 is provided, has an output hole 82 through which sound waves from the sounding body 2 are output. The sound wave sensor 1 also includes a second casing 84 including a surface opposed to the surface of the first casing 81 in which the output hole 82 is formed and having an input hole 83 through which sound waves output from the output hole 82 are input. The second casing 84 functions as an echo body 3.

The sound wave sensor 1 according to the present embodiment can be in a small size such as about 2 cm, and it is necessary to cause the banknote 4 to pass through the gap therein. This means that it is necessary to allow the resonance characteristic to be changed while securing a distance between the sounding body 2 and the banknote 4 to some extent within a narrow range. Thus, by storing the sounding body 2 in the first casing 81 as illustrated in FIG. 8, it is possible to stably secure a distance between the sounding body 2 and the banknote 4. Further, since sound waves from the sounding body 2 are output to a space which is closed to some extent in the first casing 81 and the second casing 84, it is less likely to be affected by the noise from the outside, whereby it is possible to measure the resonance characteristic accurately.

It should be noted that while a sheet-like medium is limited to a banknote in the description given in the respective embodiment, a sound wave sensor of the present invention can be used for detecting a paper medium such as a paper sheet, a postcard, or a business card, various types of cards, or the like. In particular, regarding a sheet-like medium having transparency or reflectivity with respect to light (for example, transparent vinyl, fabric having transparency, mirrors, those having a surface covered with aluminum foil, or the like), an error may occur in an optical sensor. However, by using a sound wave sensor of the present invention, it is possible to accurately detect such a medium one by one.

REFERENCE SIGNS LIST 1 sound wave sensor
2 sounding body
3 echo body
4 banknote
5 slit
6 resonance determination unit
51 oscillator
52 piezoelectric element
53 resistance
54 amplifier circuit
55 filter circuit
71 microphone
81 first casing
82 output hole
83 input hole
84 second casing

The invention claimed is:

1. A sound wave sensor comprising:
a sounding body that outputs a constant sound wave signal of a predetermined frequency;
an echo body that reflects the sound wave signal output from the sounding body, the echo body being opposed to the sounding body in a direction in which the sounding body outputs the sound wave signal, and the echo body being provided at a position where the sound wave signal resonates at the predetermined frequency;
a slit through which a sheet-like medium passes, the slit being provided between the sounding body and the echo body; and
determination means for determining a resonant state of the predetermined frequency output from the sounding body.

2. The sound wave sensor according to claim 1, wherein the determination means determines the resonant state by detecting variation in power consumption of the sounding body.

3. The sound wave sensor according to claim 1, further comprising
a microphone provided near the sounding body, the microphone receiving the sound wave signal output from the sounding body, wherein
the determination means determines the resonate state based on a sound pressure of a signal detected by the microphone.

4. The sound wave sensor according to claim 1, further comprising
a first casing for accommodating the sounding body, wherein
an output hole through which the sound wave from the sounding body is output is formed in a surface opposed to a surface to which the sounding body is provided in the first casing.

5. The sound wave sensor according to claim 4, further comprising
a second casing opposed to the surface of the first casing in which the output hole is formed, the second casing having a surface having an input hole through which the sound wave output from the output hole is input, the second casing functioning as the echo body.

6. The sound wave sensor according to claim 1, wherein the sound wave is an ultrasonic wave.

* * * * *